United States Patent [19]

Strazzolini et al.

[11] Patent Number: 4,725,668

[45] Date of Patent: Feb. 16, 1988

[54] PROCESS FOR TRANSFORMING TEICOPLANIN FACTOR $A_2$ COMPONENT 1 INTO TEICOPLANIN FACTOR $A_2$, COMPONENT 3

[75] Inventors: Paolo Strazzolini, Fiume Veneto; Bruno Cavalleri, Milan, both of Italy

[73] Assignee: Gruppo Lepetit S.p.A., Italy

[21] Appl. No.: 703,647

[22] Filed: Feb. 21, 1985

[30] Foreign Application Priority Data

Feb. 21, 1984 [IT] Italy ................ 19730A/84

[51] Int. Cl.$^4$ .......................... C07K 5/12; C07H 15/24
[52] U.S. Cl. .................................. 530/317; 536/18.1
[58] Field of Search ..................... 530/317; 536/18.1

[56] References Cited

U.S. PATENT DOCUMENTS 4,629,781 12/1986 Strazzolini et al. ............... 530/317

FOREIGN PATENT DOCUMENTS 0055069 12/1981 European Pat. Off. .
0119574 3/1984 European Pat. Off. .
0119575 3/1984 European Pat. Off. .

OTHER PUBLICATIONS

M. R. Bardone, M. Paternoster & C. Coronelli, *The Journal of Antibiotics*, 31(3), pp. 170, Mar. 1978.
J. C. J. Barna et al., *Journal of The American Chemical Society*, 106(17), pp. 4895–4902, Aug. 22, 1984.
A. Malabarba et al., *The Journal of Antibiotics*, 37(9), pp. 988–999, Sep. 1984.

*Primary Examiner*—Delbert R. Phillips
*Attorney, Agent, or Firm*—Stephen L. Nesbitt; J. Michael Dixon

[57] ABSTRACT

The present invention refers to a process for transforming teicoplanin factor $A_2$ component 1 into teicoplanin factor $A_2$ component 3 by means of a chemical reaction which includes the catalytical hydrogenation of the substrate.

11 Claims, No Drawings

PROCESS FOR TRANSFORMING TEICOPLANIN FACTOR A₂ COMPONENT 1 INTO TEICOPLANIN FACTOR A₂, COMPONENT 3

The present invention refers to a process for transforming teicoplanin factor $A_2$ component 1 into teicoplanin factor $A_2$ component 3 by means of a chemical reaction.

Teicoplanin is the international non-proprietary name (INN) of the antibiotic substance formerly named teichomycin which is obtained by cultivating the strain *Actinoplanes teichomyceticus* ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the other factors by means of column chromatography on Sephadex ®.

British Patent Application Publication No. 2121401 discloses that antibiotic Teichomycin $A_2$ actually is a mixture of five closely related co-produced main components. This British application also reports the biological activities of these components. From these data it appears that the isolated components possess higher antimicrobial activity than the parent teicoplanin $A_2$ complex. In particular, teicoplanin $A_2$ component 3 is more active than teicoplanin $A_2$ component 1 in in vitro and in vivo experiments. The antimicrobial data of the five components in in vitro experiments which are disclosed in British patent application No. 2121401 are reported in the following Table I

TABLE I

| In vitro antibacterial activity of Teicoplanin A₂ component 1 and 3. | | | |
|---|---|---|---|
| | No. of tested strains | MIC (µg/ml) | |
| Microorganism | | Teicplanin A₂ Component 1 | Teicoplanin A₂ Component 3 |
| *Staphylococcus aureus* | 5 | 0.8–1.6 | 0.4–0.8 |
| *Staphylococcus epidermides* | 4 | 0.2–1.6 | 0.2–0.8 |
| *Streptococcus pyogenes* | 7 | 0.05–0.1 | 0.025–0.05 |
| *Streptococcus pneumoniae* | 6 | 0.1–0.2 | 0.05–0.1 |
| *Streptococcus faecalis* | 5 | 0.2–0.4 | 0.1–0.2 |
| *Streptococcus mitis* | 1 | 0.025 | 0.0125 |

TABLE I-continued

| In vitro antibacterial activity of Teicoplanin A₂ component 1 and 3. | | | |
|---|---|---|---|
| | No. of tested strains | MIC (µg/ml) | |
| Microorganism | | Teicplanin A₂ Component 1 | Teicoplanin A₂ Component 3 |
| *Streptococcus salivarius* | 1 | 0.2 | 0.1 |
| *Streptococcus sanguis* | 1 | 0.1 | 0.1 |
| *Streptococcus bovis* | 1 | 0.4 | 0.2 |
| *Streptococcus agalactiae* | 1 | 0.1 | 0.05 |

According to recent structural studies, it is possible to represent teicoplanin $A_2$ (formerly Teichomycin $A_2$) main components 1, 2, 3, 4 and 5 by the following formula I wherein A is N-[($C_{10}$–$C_{11}$)aliphatic acyl]-β-D-glucosaminyl group, B is a N-acetyl-β-D-glucosaminyl group and Z is a β-D-mannosyl group. All these sugar moieties, when present, are linked to the teicoplanin nucleus through O-glycosidic bonds. In the case of teicoplanin $A_2$ component 1 the ($C_{10}$–$C_{11}$) aliphatic acyl is (Z)-4-decenoic acid while in the case of teicoplanin $A_2$ component 3 is n-decanoic acid.

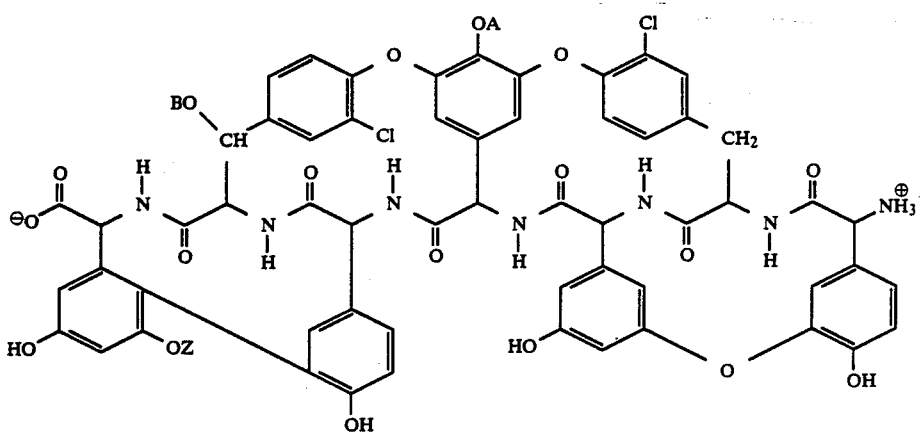

As already said, the known methods for preparing teicoplanin $A_2$ and its components includes a microbiological process (see U.S. Pat. No. 4,239,751) and a chromatographic separation process (see U.K. No. 2121401). No chemical transformation process of a component of teicoplanin factor $A_2$ into another is so far known. As it is appreciated by those skilled in the art, it is very difficult to conduct any selective process on a structurally complex substrate like the present ones in view of the presence of a variety of different functional groups which may be altered at the reaction conditions.

Surprisingly, it has been found that it is possible to selectively transform teicoplanin $A_2$ component 1 into teicoplanin $A_2$ component 3 through a chemical process which includes catalytically hydrogenating teicoplanin $A_2$ component 1 either isolated as a single product or in any mixture.

An example of a mixture which contains teicoplanin $A_2$ component 1 is the teicoplanin complex as obtained from *Actinoplanes teichomyceticus* ATCC 31121 substantially as described in U.S. Pat. No. 4,239,741.

The hydrogenation catalyst of the process of the invention is a "poisoned" hydrogenation catalyst such as Palladium on Barium sulfate, Platinum on Barium sulfate, the Lindlar catalyst (Palladium on calcium carbonate poisoned with lead), and 5% (w/w) Palladium sulfide on carbon. The preferred catalyst is Palladium on Barium sulfate. This catalyst is preferably used at a concentration between 5% and 20% (w/w) (i.e. from 5% to 20% Palladium on Barium sulfate), 5% and 10% Palladium on Barium sulfate being the most preferred. 10% Palladium on Barium sulfate is preferably employed when the reaction is conducted at room pressure and temperature, while 5% Palladium on Barium sulfate is preferably employed when the reaction is conducted at room temperature and at a pressure of 5 atm. The proportion between the substrate to be hydrogenated (teicoplanin $A_2$ component 1) and the catalyst may vary considerably. In general, these substances are contacted, on a weight to weight basis, in a proportion from 1 : 10 to 1.5 : 1, (catalyst to substrate) depending also on the specific characteristics of the selected catalyst and reaction conditions.

Generally a ratio between 0.8 to 1 and 1.2 to 1 (catalyst to substrate, w/w) is preferred while in some instances a 1 to 1 (w/w) ratio is the preferred. Even if poisoned catalyst give a very satisfactory result, it is possible to conduct the process of the invention also by using non-poisoned catalyst (e.g. 5% or 10% Palladium on carbon) in low amounts compared to the amounts of the substrate to be hydrogenated (e.g. a ratio (w/w) between 1 : 20 and 1 : 10).

The reaction solvent is water and/or a water miscible polar organic solvent such as a ($C_1$–$C_4$)alkanol or a glycol or polyglycol ether such 2-methoxyethanol. Representative and preferred examples of ($C_1$–$C_4$)alkanols are methanol and ethanol.

The preferred reaction solvent is a mixture water/methanol or water/ethanol in a ratio from 20 : 80 to 30 : 70 (v/v).

The reaction pressure is generally an important parameter in hydrogenation reactions. In general it is related to the type and concentration of the hydrogenation substrate, catalyst and reaction temperature. In the present case it may be between ambient pressure and 5 atm (490332.5 Pa). In fact, since very high yields are already obtained at ambient pressure or with a slight hydrogen overpressure (from 1 to 1.5 atm) a pressure higher than 5 atm is in general not necessary.

As for the reaction temperature, good results are conveniently obtained by operating at room temperature. Depending on the specific reaction conditions, i.e. type and concentration of the catalyst and solvent, it may be possible or convenient to use higher or lower temperatures.

As it is appreciated by those skilled in the art, the reaction time considerably varies depending on the substrate and the specific reaction conditions. In general the hydrogenation reaction is completed in 1 to 5 or 6 h. In any case, however, the reaction course may be monitored by TLC or HPLC techniques as known in the art. For instance, samples may be drawn at intervals and assayed in order to determine when the reaction is complete. The reaction may then be stopped in order to prevent the negative consequences of a prolonged contact between the final product and the reaction mass. A complementary or alternative procedure for evaluating the reaction time and the end of the hydrogenation process is based on the measure of the absorption of hydrogen by the reaction mass. The quantitative transformation of teicoplanin $A_2$ component 1 into teicoplanin $A_2$ component 3 requires in fact, 1 mole of hydrogen per mole of substrate. On the basis of this information the skilled technician is capable of controlling the reaction time and ascertain when the reaction is complete.

Once the reaction is completed, the reaction product is isolated according to known per se techniques. Tipically, the catalyst is separated by filtration. The recovered catalyst is washed troughly and the all filtrates are combined. These liquids contain the reaction product which is then recovered and purified according to known methods such as extraction with solvents, precipitation by addition of non-solvents, column chromatography and the like. Sometimes, it may be convenient to concentrate the filtrates to a small volume, precipitate the crude reaction product, redissolve it in water, clear the solution with some drop of a mineral acid, adjust the pH to about 6.0–6.5 with a strong base, and precipitate the product by adding a non-solvent. Examples of strong bases are alkali metal hydroxides such as sodium or potassium hydroxide, sodium carbonate, and ammonia. The preferred strong base is an aqueous solution of sodium hydroxide. Examples of non-solvents are ethyl ether, chloroform, benzene, hexane, acetonitrile, ethyl acetate, acetone and carbon tetrachloride, ethyl ether being the preferred for precipitation purposes. Sometimes, by operating in this way, a suspension form which can be filtered with difficulty. A filtrable solution may then be obtained by adding a water-immiscible non-solvent such as butanol that separate the product at the interface between the aqueous and organic layers. According to another procedure, the reaction product if recovered from the aqueous solution adjusted at pH 6.0–6.5 by means of the "salting-out" procedure.

This procedure, as known in the art, is characterized by the addition of a suitable salt, tipically ammonium sulfate, to the solution of the product until it precipitates because of the change of the ionic strength of the solution. Also in this case, like in the foregoing precipitation procedure, the precipitation of the product (teicoplanin $A_2$ component 3) may be facilitated by adding small particles of pure teicoplanin $A_2$ component 3 or other suitable precipitation primer.

Physico chemical characteristics of teicoplanin $A_2$ factor 1

Teicoplanin $A_2$ factor 1 is a white amorphous powder that upon heating begins to darken at about 220° C. and is completely decomposed at 255° C., which has the following characteristics:

(a) It is freely soluble in water at pH>7.0 or at pH<2, in dimethylformamide, dimethylsulfoxide, and propyleneglycol; slightly soluble in methylcellosolve and glycerol; poorly soluble in methanol and ethanol, almost insoluble in chloroform, benzene, n-hexane, acetonitrile, ethyl ether, acetone, ethyl acetate, carbon tetrachloride (b) has an ultraviolet absorption spectrum, that exhibits the following absorption maxima:

in 0.1 N hydrochloric acid: $\lambda_{max}$ 278 nm ($E_{1cm}^{1\%} = 49.5$)

in phosphate buffer pH 7.4 : $\lambda_{max}$ 278 nm ($E_{1cm}^{1\%} = 50.0$)

in 0.1 N sodium hydroxide: $\lambda_{max}$ 297 nm ($E_{1cm}^{1\%} = 72.1$)

(c) an infrared absorption spectrum in nujol, with the following absorption maxima: 3700–3100, 2960–2840 (nujol), 1645, 1590, 1510, 1460 (nujol), 1375 (nujol), 1305, 1230, 1180, 1155, 1060, 1025, 970, 890, 845, 815, 720 (nujol);

(d) an elemental analysis, after the sample has been previously dried at about 140° C. under inert atmosphere (%Δw=8.5), which indicated the following approximate percentage composition (average): carbon 56.70%; hydrogen, 4.90%; nitrogen 6.65%; chlorine 3.80%; oxygen (by difference), 27.95%;

(e) a retention time ($t_R$) of 21.2 minutes when analyzed by reverse phase HPLC using a 5 um Zorbax ® ODS column (4.6×150 mm), and eluting with a linear gradient from 0% to 50% solution B in solution A in 40 minutes [solution A: 25 mM $NaH_2PO_4$/acetonitrile (9/1, v/v), buffered at pH 6.0 with 0.1 N NaOH; solution B: 25 mM $NaH_2PO_4$/acetonitrile (3/7) buffered at pH 6.0 with 0.1 N NaOH], with a flow rate of 2 ml/min.; (internal standard: 3,5-dihydroxy toluene $t_R$ 8.84 minutes)

(f) the following groups of signals in the 270 MHz $^1H$ NMR spectrum registered in DMSO-$d_6$ with the addition of a few drops of $D_2O$ (conc. 25 mg/0.5 ml) (TMS as internal standard: δ=0.00 ppm): 0.8–1.5 (m); 1.7–2.3 (m); 2.7–4.0 (m); 4.0–4.7 (m) 4.8–5.8 (m); 6.2–8.1 (m)

(g) an acidic function capable of forming salts (h) a basic function capable of forming salts (g) a molecular weight of about 1875 as determined by mass spectrometric analysis using fast atom bombardment (FAB) as the ion source (for a presentation of FAB mass spectrometry, see for instance M. Barber et al. Nature, 293, 270–75 (1981)).

Physico chemical characteristics of teicoplanin $A_2$ factor 3.

Teicoplanin $A_2$ factor 3 is a white amorphous powder that upon heating begins to decompose at 205° C. and is completely decomposed at 250° C., which has the following characteristics:

(a) It is freely soluble in water at pH>7.0 or at pH<2, in dimethylformamide, dimethylsulfoxide, and propyleneglycol; slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride (b) an ultraviolet absorption spectrum, that exhibits the following absorption maxima:

in 0.1 N hydrochloric acid: $\lambda_{max}$ 278 nm ($E_{1cm}^{1\%}$=49.2)

in phosphate buffer pH 7.4: $\lambda_{max}$ 278 nm ($E_{1cm}^{1\%}$=50.8)

in 0.1 N sodium hydroxide: $\lambda_{max}$ 297 nm ($E_{1cm}^{1\%}$=72.7)

(c) an infrared absorption spectrum in nujol with the following observable absorption maxima: 3700–3100, 2960–2850 (nujol); 1645, 1590, 1510, 1460 (nujol), 1375 (nujol); 1300, 1230, 1180, 1150, 1120, 1060, 1030, 970, 890, 845, 820, 800, 720 (nujol)

(d) an elemental analysis, after the sample has been previously dried at about 140° C. under inert atmosphere (%Δw=12.0) which indicated the following approximate percentage composition (average): carbon, 56.26%; hydrogen, 5.20%; nitrogen, 6.69%; chlorine, 3.95%; oxygen (by difference), 27.90%

(e) a retention time ($t_R$) of 23.3 minutes when analyzed by reverse phase HPLC using a 5 um Zorbax ® ODS column (4.6×150 mm) and eluting with a linear gradient from 0% to 50% solution B in solution A in 40 minutes [solution A: 25 mM $NaH_2PO_4$/acetonitrile (9/1, v/v), buffered at pH 6.0 with 0.1 N NaOH; solution B: 25 mM $NaH_2PO_4$/acetonitrile (3/7, v/v), buffered at pH 6.0 with 0.1 N NaOH], with a flow rate of 2 ml/min; (internal standard: 3,5-dihydroxytoluene $t_R$ 8.84 minutes)

(f) the following groups of signals in 270 MHz $^1H$ NMR spectrum registered in DMSO-$d_6$ with the addition of a few drops of $D_2O$ (conc. 25 mg/0.5 ml) (TMS as internal standard: δ=0.00 ppm): 0.7–1.5 (m); 1.8–2.0 (m); 2.7–4.5 (m); 4.6–5.7 (m); 6.2–8.0 (m)

(g) an acidic function capable of forming salts (h) a basic function capable of forming salts (i) a molecular weight of about 1877 as determined by FAB mass spectrometry.

The following examples further illustrate the invention and should not construed as limiting its overall scope.

EXAMPLE 1

Hydrogenation of Teicoplanin (Disappearance of the peak corresponding to teicoplanin factor $A_2$ component 1 and increase of the peak corresponding to teicoplanin factor $A_2$ component 3).

A suspension of 2 g of teicoplanin (HPLC composition teicoplanin $A_2$ component 1=13.1%, teicoplanin $A_2$ component 3=19.3%, other teicoplanin components 67.3%) in water/methanol 70:30 (v/v), (250 ml) is clarified by adding a few drops of 1 N hydrochloric acid. This mixture is then submitted to catalytical hydrogenation in the presence of 5% Palladium on Barium sulfate (2 g) at room temperature and ambient pressure.

The reaction course is monitored by controlling the amount of hydrogen which is absorbed and by TLC or HPLC procedure.

After about 2 h, the HPLC analysis shows an almost quantitative transformation of teicoplanin $A_2$ component 1 into teicoplanin $A_2$ component 3. The catalyst is then separated by filtration, washed with methanol/water and then methanol (250 ml). The filtrates are pooled and the solvents evaporated under vacuum at about 40° C. The residue is then resuspended in water (50 ml), this solution is adjusted to pH 6.0–6.5 with 1 N NaOH. n-Butanol (100 ml) is added to the suspension which forms, and after stirring for about 30 min, the mixture is centrifuged.

At the interface between the two phases a solid forms which is recovered by filtration, washed with a little amount of methanol then with ethyl ether and air-dried to give 1.8 g of teicoplanin (HPLC composition : teicoplanin factor $A_2$ component 1 absent; teicoplanin factor $A_2$ component 3=32.0%, other teicoplanin components 67.9%).

EXAMPLE 2

Transformation of pure Teicoplanin $A_2$ component 1 into pure teicoplanin $A_2$ component 3.

A suspension of teicoplanin $A_2$ component 1 (200 mg) in water/methanol 70 : 30 (25 ml) is clarified by adding a few drops of 1 N hydrochloric acid. This mixture is then submitted to catalytical hydrogenation in the presence of 10% Palladium on Barium sulfate (0.2 g) at room temperature and ambient pressure.

The reaction course is monitored by controlling the amount of hydrogen which is absorbed and by TLC or HPLC procedure.

After about 2 h, the HPLC analysis shows an almost quantitative transformation of teicoplanin $A_2$ component 1 into teicoplanin $A_2$ component 3. The catalyst is then separated by filtration, washed with methanol/water and then methanol (25 ml). The filtrates are pooled and the solvents evaporated under vacuum at about 40° C. The residue is then resuspended in water (10 ml), this solution is adjusted to pH 6.0–6.5 with 1 N NaOH. n-Butanol (10 ml) is added to the suspension which forms, and after stirring for about 30 min, the mixture is centrifuged.

At the interface between the two phases a solid forms which is recovered by filtration, washed with a little amount of methanol then with ethyl ether and air-dried to give 170 mg of teicoplanin factor $A_2$ component 3 (Yield 85%).

EXAMPLE 3

A solution of 100 mg of teicoplanin (HPLC composition teicoplanin $A_2$ component 1=13.1%, teicoplanin $A_2$ component 3=19.3%, other teicoplanin components 67.7%) in 10 ml of 30% aq MeOH is hydrogenated at 5 atm and room temperature in the presence of 100 mg of 5% Pd on $BaSO_4$. After 6 hours of stirring, 100 mg of the catalyst is added and the reaction mixture is stirred under hydrogen for another 2 hours. The reaction mixture is then filtered, and worked up as in the foregoing example 1, obtaining 90 mg of teicoplanin (HPLC composition : teicoplanin $A_2$ component 1=1.8%, teicoplanin $A_2$ component 3=31.6%, other teicoplanin components 66.5%).

We claim:

1. A process for transforming teicoplanin factor $A_2$ component 1 into teicoplanin factor $A_2$ component 3 which comprises catalytically hydrogenating teicoplanin factor $A_2$ component 1, either pure or in a mixture containing it, in the presence of a poisoned catalyst, and in water and/or water miscible polar organic solvent.

2. A process according to claim 1 wherein the mixture containing teicoplanin factor $A_2$ component 1 is a teicoplanin complex and the obtained product is a teicoplanin complex enriched in teicoplanin factor $A_2$ component 1.

3. A process according to claim 1 wherein the poisoned catalyst is Palladium on Barium sulfate.

4. A process according to claim 1 wherein the poisoned catalyst is Palladium on Barium sulfate at a concentration between 5% and 15% (w/w).

5. A process according to claim 1 wherein the poisoned catalyst is 10% Palladium on Barium sulfate.

6. A process according to claim 1 wherein the solvent is a mixture water/methanol or water/ethanol.

7. A process according to claim 1 wherein the solvent is a mixture water/methanol or water/ethanol in a ratio from 20:80 to 30:70 (v/v).

8. A process according to claim 1 wherein the reaction pressure is between ambient pressure and 5 atm.

9. A process according to claim 1 wherein the reaction pressure is ambient pressure.

10. A process according to claim 1 wherein the reaction temperature is room temperature.

11. A process according to claim 1 wherein the isolation of the reaction product includes:
    (a) separating the catalyst by filtration, and collecting the filtrate which contains the reaction product
    (b) washing the recovered catalyst with the reaction solvent and combining this filtrates with the filtrate of step (a)
    (c) concentrate the pooled filtrates to a small volume or to dryness under reduced pressure
    (d) dissolve the obtained solid in water
    (e) after having clarified the solution with a few drops of mineral acid, adjust the pH to 6.0–6.5
    (f) collect the precipitate by filtration after having added a non-solvent, if necessary.

* * * * *